United States Patent
Al-Kassim et al.

(10) Patent No.: US 6,904,630 B2
(45) Date of Patent: Jun. 14, 2005

(54) TABLETOP FOR RADIATION THERAPY AND DIAGNOSTIC IMAGING

(75) Inventors: Adil Al-Kassim, Svendborg (DK); Gary Gearon, Shohola, PA (US)

(73) Assignee: Siemens Medical Solutions USA, Inc., Iselin, NJ (US)

( * ) Notice: Subject to any disclaimer, the term of this patent is extended or adjusted under 35 U.S.C. 154(b) by 26 days.

(21) Appl. No.: 09/898,272

(22) Filed: Jul. 2, 2001

(65) Prior Publication Data

US 2002/0095730 A1 Jul. 25, 2002

Related U.S. Application Data

(60) Provisional application No. 60/219,998, filed on Jul. 21, 2000.

(51) Int. Cl.[7] .............................................. A61B 6/04
(52) U.S. Cl. ........................... 5/601; 600/410; 378/209
(58) Field of Search ........................... 5/601, 600, 607; 378/209; 600/415

(56) References Cited

U.S. PATENT DOCUMENTS

| | | | | |
|---|---|---|---|---|
| 3,428,307 A | * | 2/1969 | Hunter et al. .................... | 5/601 |
| 3,763,375 A | | 10/1973 | Scheninger | |
| 3,868,103 A | * | 2/1975 | Pageot et al. ................ | 378/209 |
| 3,897,345 A | | 7/1975 | Foster | |
| 3,947,686 A | * | 3/1976 | Cooper et al. .................. | 5/601 |
| 4,146,793 A | | 3/1979 | Bergstrom et al. | |
| 4,568,071 A | | 2/1986 | Rice | |
| 4,575,064 A | * | 3/1986 | Menor ........................... | 5/601 |
| 4,669,136 A | * | 6/1987 | Waters et al. ................... | 5/601 |
| 5,537,454 A | | 7/1996 | Korver ........................... | 378/65 |
| 5,572,569 A | * | 11/1996 | Benoit et al. ................... | 5/601 |
| 5,577,503 A | | 11/1996 | Bonutti | |
| 5,675,851 A | * | 10/1997 | Feathers ......................... | 5/601 |
| 5,742,962 A | | 4/1998 | Yoshino et al. | |
| 5,778,047 A | | 7/1998 | Mansfield et al. ........... | 378/209 |
| 5,806,116 A | | 9/1998 | Oliver et al. ................... | 5/621 |
| 5,987,672 A | * | 11/1999 | Oosterwaal .................... | 5/601 |
| 6,003,174 A | * | 12/1999 | Kantrowitz et al. ............ | 5/601 |
| 6,161,237 A | * | 12/2000 | Tang et al. ..................... | 5/621 |
| 6,240,582 B1 | * | 6/2001 | Reinke .......................... | 5/601 |
| 6,367,104 B1 | * | 4/2002 | Falbo et al. .................... | 5/601 |
| 6,378,149 B1 | * | 4/2002 | Sanders et al. ................. | 5/601 |
| 6,560,799 B1 | * | 5/2003 | Pflaum et al. .................. | 5/600 |
| 6,615,429 B2 | * | 9/2003 | Weil et al. ..................... | 5/601 |

FOREIGN PATENT DOCUMENTS

GB      2 057 830 A      4/1981

OTHER PUBLICATIONS

Design Engineering Aug. 1990, London, GB, Carbon fibre X-ray table, XP000140563, 1 pg.

* cited by examiner

Primary Examiner—Frederick L. Lagman

(57) ABSTRACT

A tabletop device for use in supporting and positioning a patient in a medical therapy or diagnostic system having a support base and operable to project a beam over at least a portion of the tabletop. The tabletop is rotatably mounted on the support base. The tabletop includes a central section configured for attachment to the support base. The central section is positioned such that it is outside of a beam projection area when the tabletop is mounted in the medical therapy or diagnostic system. A frame is fixedly attached to the central section and extends longitudinally outward from opposite sides thereof. The tabletop further includes a support system connected to the frame for supporting a patient thereon. At least a portion of the frame and support system is located within the beam projection area when the tabletop is mounted in the medical therapy or diagnostic system and the portion of the frame located within the beam projection area is formed from substantially non-metal components.

37 Claims, 9 Drawing Sheets

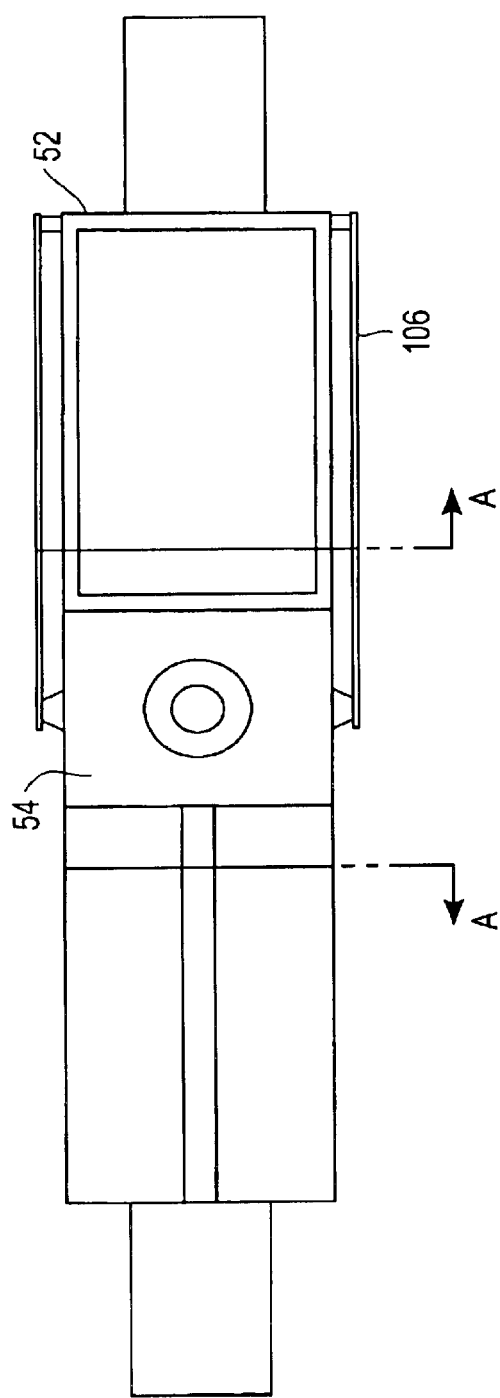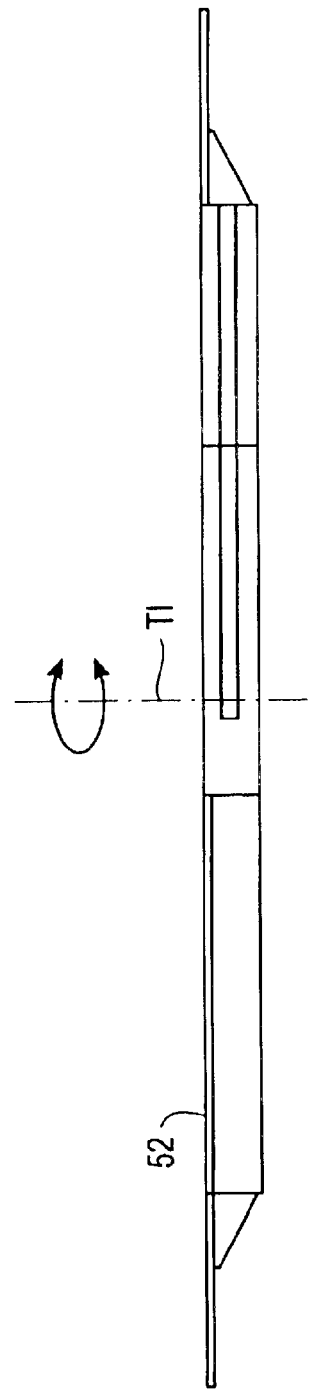
FIG. 3
FIG. 4

TABLETOP FOR RADIATION THERAPY AND DIAGNOSTIC IMAGING

RELATED APPLICATION

The present application claims the benefit of U.S. Provisional Patent Application Ser. No. 60/219,998, filed Jul. 21, 2000.

FIELD OF THE INVENTION

The present invention relates generally to radiation therapy and diagnostic imaging, and more particularly, to a tabletop system for use in radiation therapy and diagnostic imaging.

BACKGROUND OF THE INVENTION

A radiation therapy or diagnostic imaging device generally includes a gantry which can be swiveled around a horizontal axis of rotation in the course of a therapeutic treatment or diagnostic imaging. A patient is supported in a substantially rigid position on a tabletop while the patient is exposed to a radiation source or imaging is performed. In radiation therapy, an electron linear accelerator is located within the gantry for generating a high energy radiation beam for therapy. This high energy radiation beam may be an electron beam or photon (x-ray) beam, for example. During treatment, the radiation beam is trained on a zone of a patient lying in an isocenter of the gantry rotation. The radiation source is typically movable about the table so that the patient can be exposed to radiation from all possible angles so that radiation can be directed at the tumor site to destroy a tumor and minimize exposure to healthy tissue.

Linear accelerators may be used in the medical environment for a variety of applications. A beam of charged particles (e.g., electrons) from a linear accelerator may be directed at a target which is made of a material having a high atomic number, so that an x-ray beam is produced for radiation therapy. Alternatively, the beam of charged particles may be applied directly to a patient during a radio-surgical procedure. Such radiosurgery has become a well-established therapy in the treatment of brain tumors. A high-energy beam may be directed at a localized region to cause a breakdown of one or both strands of the DNA molecule inside cancer cells, with the goal of at least retarding further growth and preferably providing curative cancer treatment.

For radiation therapy, diagnostic imaging, surgery, and other medical procedures, a patient is placed on a tabletop supported by a table structure. The tabletop is typically a cantilever structure configured to position the patient in the beam area with room on the exit side for imaging equipment. For certain radiation therapy programs, a patient treatment area is immobilized for accurate radiation delivery during the course of treatment. The tabletop is used to maintain the patient in a rigid, properly aligned position to prevent harm to healthy body tissue. In treatments where immobilization is planned, this is typically done by means of a thermoplastic sheet which is custom formed over the patient and attached to an anchoring panel. In some applications, the anchoring panel rests on the tabletop with no direct physical attachment. In other applications, the anchoring panel clamps to the tabletop or attaches to plates which clamp in set positions. These techniques require the therapist to accurately reproduce a variable setup.

For typical programs, a patient may have imaging or scanning performed on one type of tabletop, simulation on another tabletop, and treatment delivered utilizing another tabletop. It is generally desired that the same tabletop construction is used throughout the treatment program so that the setup of the patient is consistent throughout the treatment.

For radiation therapy, imaging, simulation, and delivery, it is desirable for the patient support tabletop surface to be generally planar and rigid to provide accuracy and repeatability. It is also desirable for a tabletop surface to have a minimum effect on radiation transmission in order to maintain high imaging and beam quality, as well as minimize loss of deliverable dose and skin sparing for treatments that are directed through the tabletop structure before reaching the patient.

High rigidity has typically been achieved by panels with a thickness of one cm or greater. One drawback to these structures is that they typically do not have acceptable transmission or skin sparing properties required for certain types of treatments. High transmission factors have typically been achieved by a mesh grid work or "racquet", constructed with a woven pattern. However, these tabletop designs often do not provide an acceptable rigidity to provide consistent positioning and patient support. In order to overcome strength and rigidity problems, conventional tabletops typically include metal components within the tabletop structure to increase strength and rigidity or provide fastener support for tabletop attachments. The metal components often interfere with the treatment or diagnostics since they impact transmission and appear as artifacts in imaging. The metal tabletop structure may also block some of the radiation rays or attenuate the radiation, resulting in inaccurate dosing. This may occur even if the material of the tabletop is not metal but has significant thickness, such as with a composite sandwich design.

There is, therefore, a need for a tabletop system that provides acceptable strength and rigidity without interfering with the treatment or imaging performed on the patient.

Furthermore, conventional patient positioning devices include immobilization devices that are positioned on top of the surface of the tabletop and require locking to the surface or alignment to lateral and independent positioning lasers, as well as, placement and replacement of the accessory immobilization devices to the surface of the diagnostic and treatment tabletops. These immobilization devices are often heavy and difficult to position on the tabletop. It is therefore, desirable to have immobilization devices that are integrated into the tabletop design, thus reducing the need for repeated positioning of the devices on the tabletop.

SUMMARY OF THE INVENTION

A tabletop device for use in supporting and positioning a patient in a medical therapy or diagnostic system is disclosed. The medical therapy or diagnostic system includes a support base and is operable to project a beam over at least a portion of the tabletop. The tabletop is rotatably mounted on the support base and includes a central section configured for attachment to the support base. The central section is positioned such that it is outside of a beam projection area when the tabletop is mounted in the medical therapy or diagnostic system. A frame is fixedly attached to the central section and extends longitudinally outward from opposite sides thereof. The tabletop further includes a support system connected to the frame for supporting a patient thereon. At least a portion of the frame and support system is located within the beam projection area when the tabletop is mounted in the medical therapy or diagnostic system and the portion of the frame and support system located within the beam projection area is formed from non-metal components.

The above is a brief description of some deficiencies in the prior art and advantages of the present invention. Other features, advantages, and embodiments of the invention will be apparent to those skilled in the art from the following description, drawings, and claims.

BRIEF DESCRIPTION OF THE DRAWINGS

FIG. 3 is a plan view of the tabletop of FIG. 2 with headboard extensions and accessory rails installed and an illustration of a beam area on the tabletop.

FIG. 4 is a side view of the tabletop of FIG. 3.

Corresponding reference characters indicate corresponding parts throughout the several views of the drawings.

DETAILED DESCRIPTION OF THE PREFERRED EMBODIMENTS

The following description is presented to enable one of ordinary skill in the art to make and use the invention. Descriptions of specific embodiments and applications are provided only as examples and various modifications will be readily apparent to those skilled in the art. The general principles described herein may be applied to other embodiments and applications without departing from the scope of the invention. Thus, the present invention is not to be limited to the embodiments shown, but is to be accorded the widest scope consistent with the principles and features described herein. For purpose of clarity, details relating to technical material that is known in the technical fields related to the invention have not been described in detail.

Figure 1:
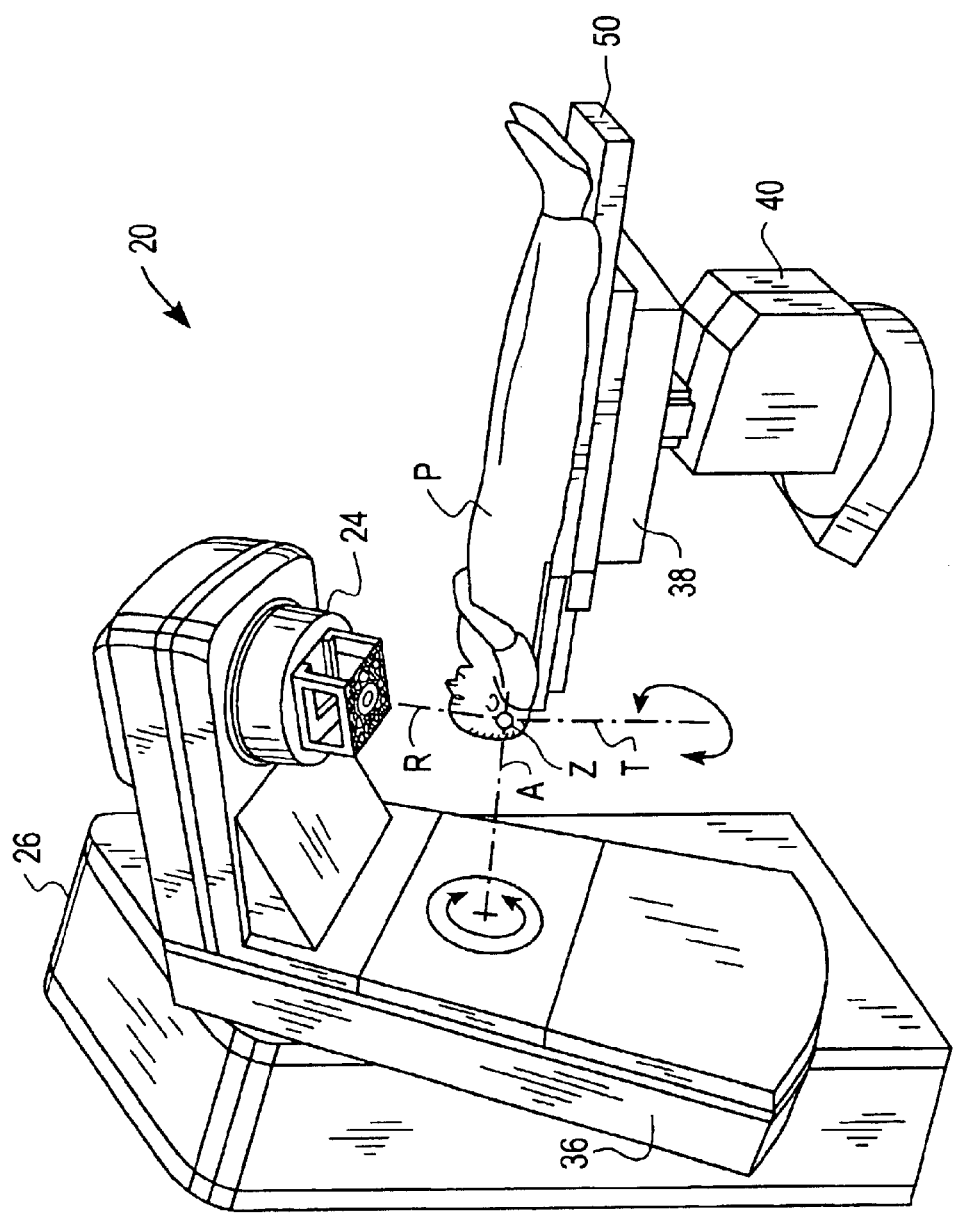
FIG. 1 is a diagram of a radiation treatment device having a tabletop according to an embodiment of the present invention and a patient positioned for treatment on the tabletop.

Referring now to the drawings, and first to FIG. 1, a radiation treatment device is shown and generally indicated at 20. The radiation treatment device 20 may include, for example, a beam shielding device within a treatment head 24, a control unit within a housing 26 connected to a treatment processing unit (not shown). The radiation treatment device further includes a gantry 36 which can be swiveled for rotation about axis A in the course of a therapeutic treatment. The treatment head 24 is fixed to the gantry 36 for movement therewith and a linear accelerator is located within the gantry for generating high powered radiation used for therapy. The radiation emitted from the linear accelerator extends generally along axis R. Electron, photon, or any other detectable radiation may be used for the therapy. During treatment, the radiation beam is focused on a zone Z of an object P (e.g., a patient who is to be treated). The zone to be treated is located at an isocenter defined by the intersection of the rotational axis A of the gantry 36, rotational axis T of treatment table 38, and the radiation beam axis R. The treatment device 20 described above is provided as an example of a device for use in delivering a treatment with a patient supported on a tabletop 50 described herein. The tabletop 50 is attached to a support base 40 and may be rotatably mounted on the fixture. The tabletop 50 may be used, for example, as an integrated immobilization tabletop and may be installed in several treatment mode applications. It is to be understood that the tabletop 50 may be connected to a diagnostic imaging device, radiation therapy simulator, or radiation therapy device different than shown herein, without departing from the scope of the invention. The support system may also be configured for use with stereotactic systems. As further described below, the tabletop 50 may be used as a support surface for a patient and an immobilization tabletop for many different treatment mode applications. Since different versions of the same tabletop are used with different treatment devices, a patient can receive all aspects of a radiation program (e.g., treatment, imaging) on the same tabletop configuration. Thus, providing improved consistency of application parameters. The tabletop 50 also provides the added benefit of being lightweight as compared to conventional treatment tabletops due to the reduced use of metal components that may cause repeated motion stress and strain to the technologist over time.

Figure 2:
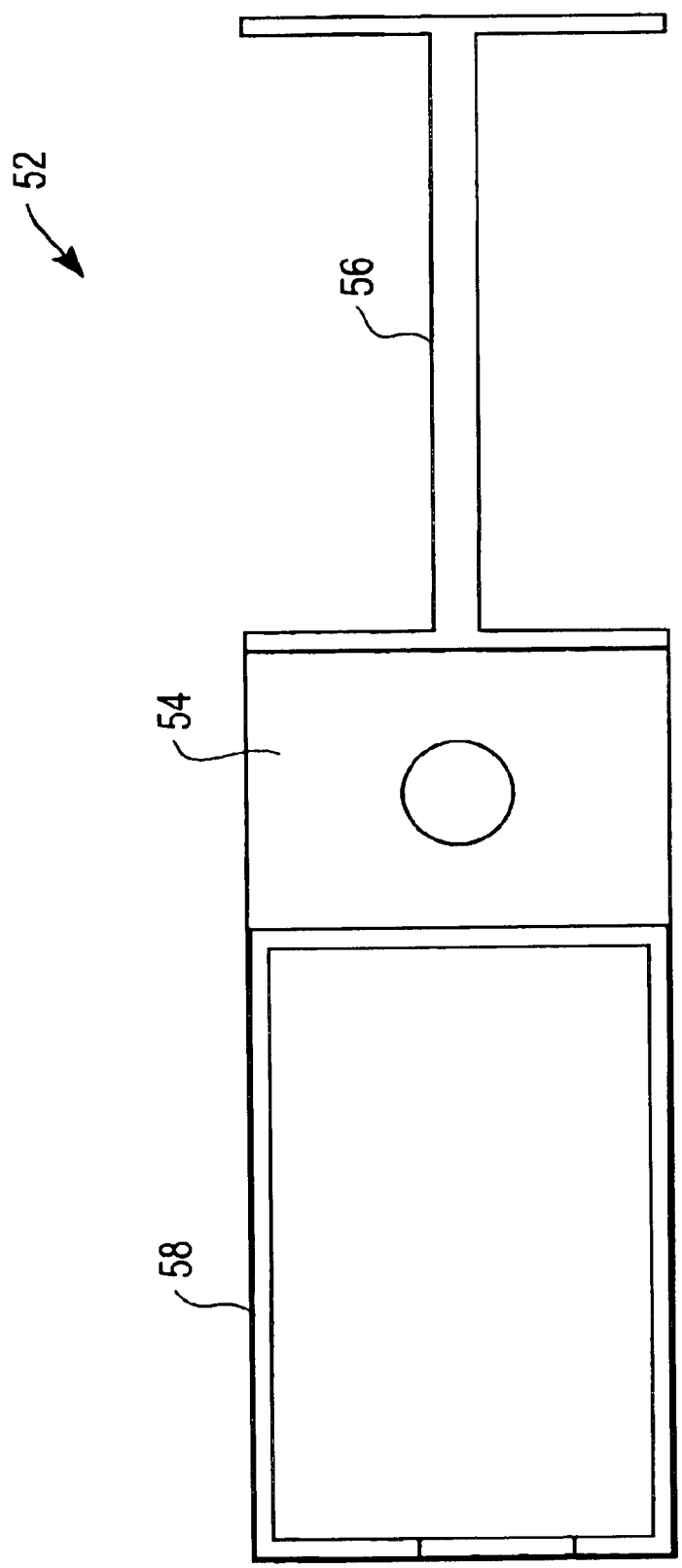
FIG. 2 is a plan view of a frame of the tabletop of the present invention.

The tabletop 50 includes a frame, generally indicated at 52 in FIG. 2, and support systems such as support platforms, head extensions, and accessory rails as shown in FIG. 3. Various types of support systems (e.g., inserts, platforms, accessories) and combinations of support systems may be connected to, inserted into, or placed into the frame, as further described below. The frame includes a generally T-shaped section 56 that extends from one end of a central section 54 and a rectangular section 58 that extends from an opposite end of the central section (FIG. 2). As shown in FIGS. 1 and 4, the tabletop is rotatably mounted on support base 40 of the treatment device about a tabletop axis T1. The beam projected from the treatment device is arranged so that it can be directed at the patient supported by the tabletop 50. The main structural components of the tabletop 50 and support systems are made of non-metal materials in the beam area (indicated by arrows A in FIG. 3). The beam area generally extends longitudinally outward from the central section 54 of the tabletop frame. Thus, metal materials are only used in the central section of the table top so that the metal components do not interfere with the therapy or imaging by the treatment or imaging device. Minor metal components such as screws or springs may be used at the peripheral of the treatment area to provide rigidity which may not be achieved by non-metallic components. The non-beam area of the tabletop may extend outward, for example, 32.5 cm from the tabletop axis T to form a 65 cm section which may contain metal components (see arrows A on FIG. 3).

Figure 5:
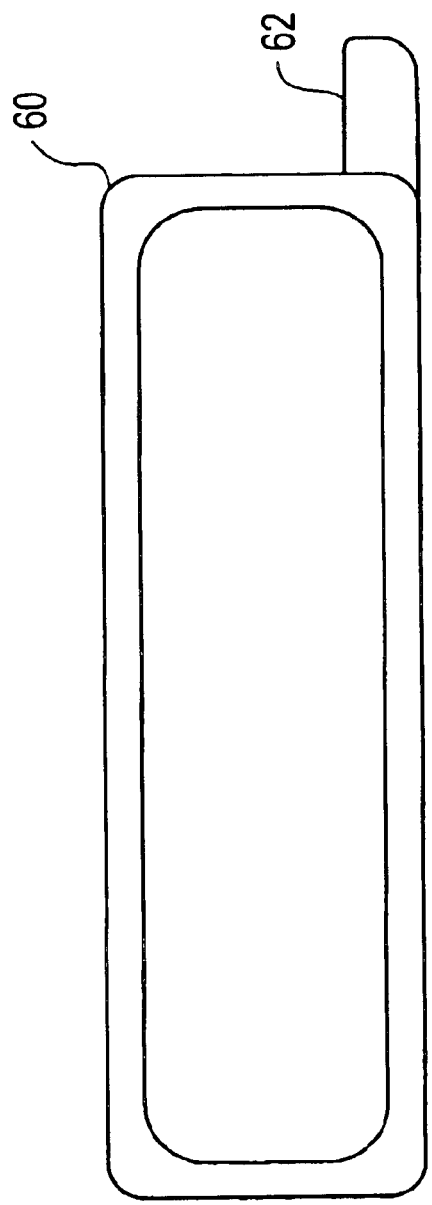
FIG. 5 is a cross-sectional view of a tubular member of the tabletop frame of FIG. 2.
Figure 6:
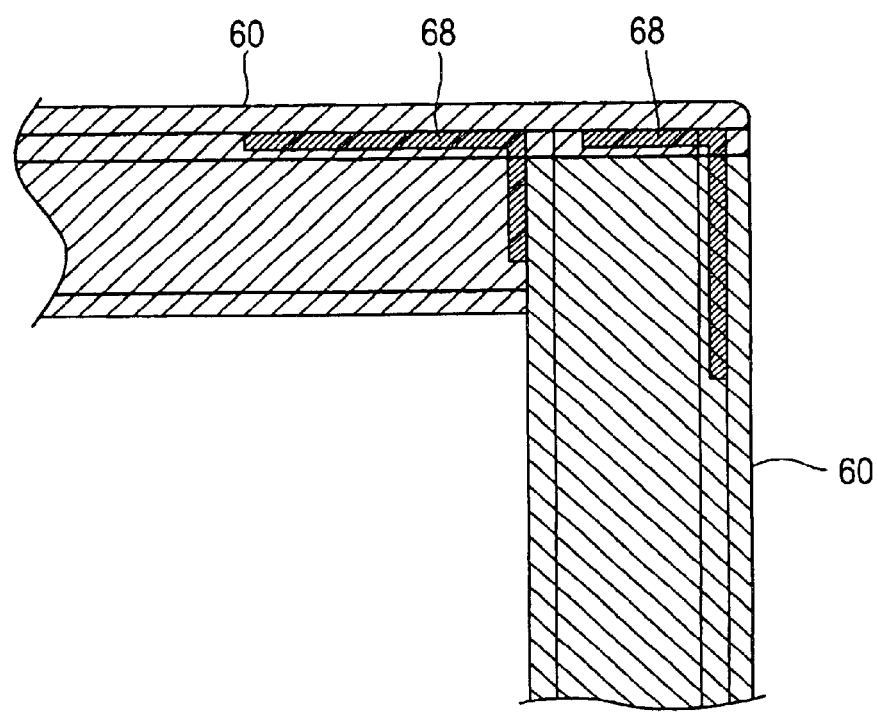
FIG. 6 is a cross-sectional partial view of a corner connection of tubular members in the tabletop frame of FIG. 2.
Figure 9:
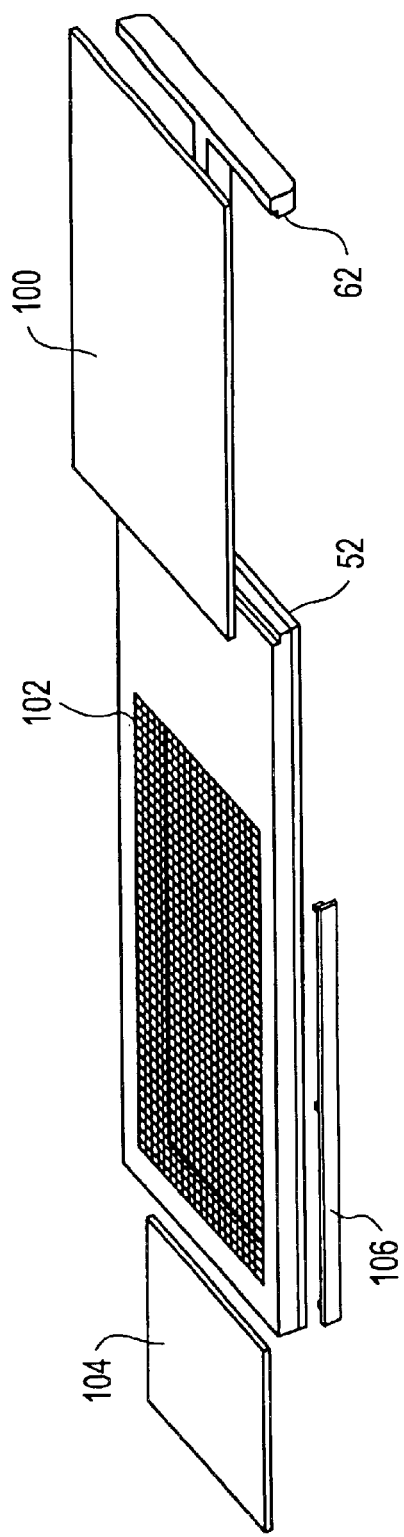
FIG. 9 is an exploded view of the tabletop showing supports that may be used with the frame of FIG. 2.

The tabletop frame 52 is constructed of generally rectangular tubular members 60 (FIG. 5). The tubular members 60 may have dimensions, for example, of 100×25×88 mm. The tubular member 60 preferably includes an integral shoulder section 62 which provides a lip for insertion of panels into the frame, as shown in FIG. 9 and described below. The tubular member 60 is formed from a non-metal material, and may be formed from a vinylester/carbon material, for example. The tubular members 60 are attached to one another with angle members 68 which are attached to inner surfaces of the tubular members (FIG. 6). The angle members 68 are also formed from composite or other non-metallic material and may be formed, for example, from carbon fiber. The angle members 68 may be glued to the inner surfaces of the tubular members 60 with Araldite 2021 or any other suitable adhesive. Mechanical means such as bolts may also be used with or without adhesives to provide further rigidity. The angle members 68 may have a dimension of 70×15×3 mm to fit within the tubular members 60 described above. Carbon fiber or other non-metallic end bushings may also be attached to the tubular members 60 for attachment of external components, as described below.

Figure 7:
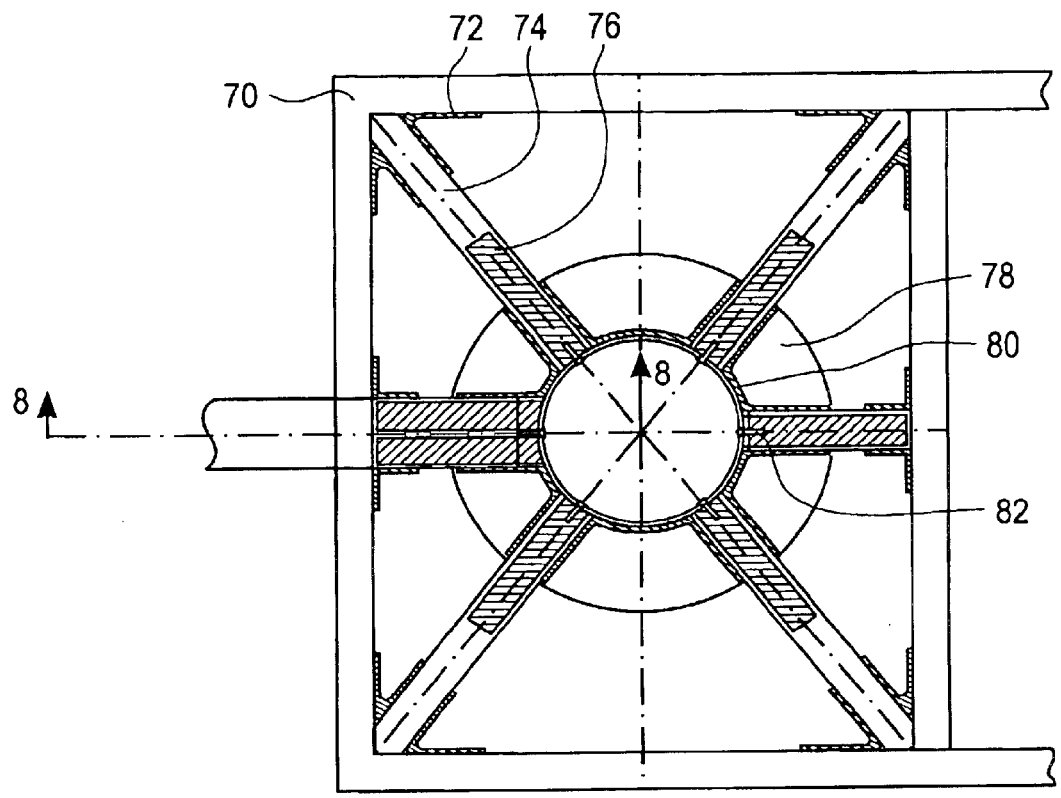
FIG. 7 is a plan view of a central portion of the frame of FIG. 2 with parts removed to show detail of a hub connection used to hold the tabletop in a fixed position relative to rotation about a tabletop stand.

As previously discussed, the central section 54 of the tabletop may include metal components since it is not within the beam projection area. The central section 54 is shown in detail in a plan view in FIG. 7 and in FIG. 8 in a cross-sectional view taken through line 8—8 of FIG. 7. The central section 54 includes an outer carbon frame 70 and a hub and spoke arrangement configured to rotatably mount on the support base of the treatment device. The hub and spokes are attached to the outer frame 70 with prefabricated carbon angles 72 which are glued to the frame with an adhesive, such as Araldite 2021 or other suitable attachment means. Carbon profile tubes 74 are connected to the angles 72 and sized to receive spokes 76 extending from central hub 78. The carbon tubes 72 are fixedly attached to prefabricated carbon angles 80 interposed between the tubes and central hub 78. The spokes 76 are preferably metal (e.g., stainless steel) to provide adequate strength and rigidity. The spokes 74 are mounted on the hub 78, which is also formed of a metal such as steel, and are fixedly attached to the hub with screws 82.

Figure 8:
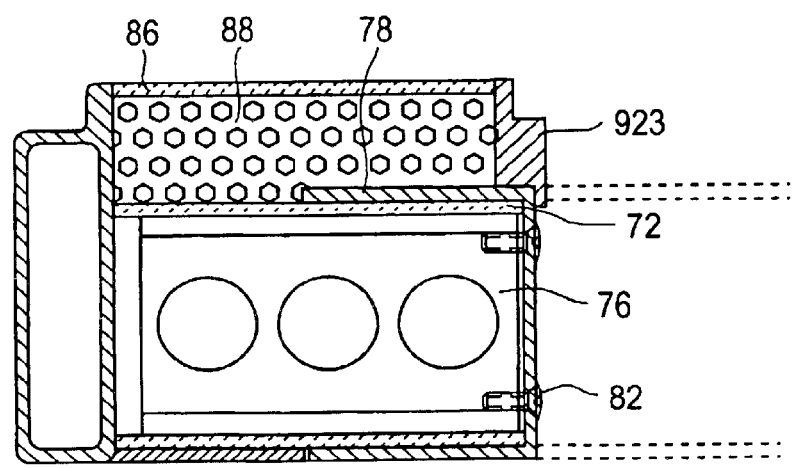
FIG. 8 is a cross-sectional view taken through line 8—8 of FIG. 7.

FIG. 8 illustrates a cross-sectional view of one half of the central section 54. At one end is the carbon outer frame 70 which is attached to a carbon skin 86, which may have a thickness of 4 mm, for example. The carbon skin is filled with a filler 88, such as Rohacell 71, or any other suitable filler material. At the opposite end of the skin 86 is an aluminum ring 92. The hub 78 is attached to the carbon tube 72.

Figure 10:
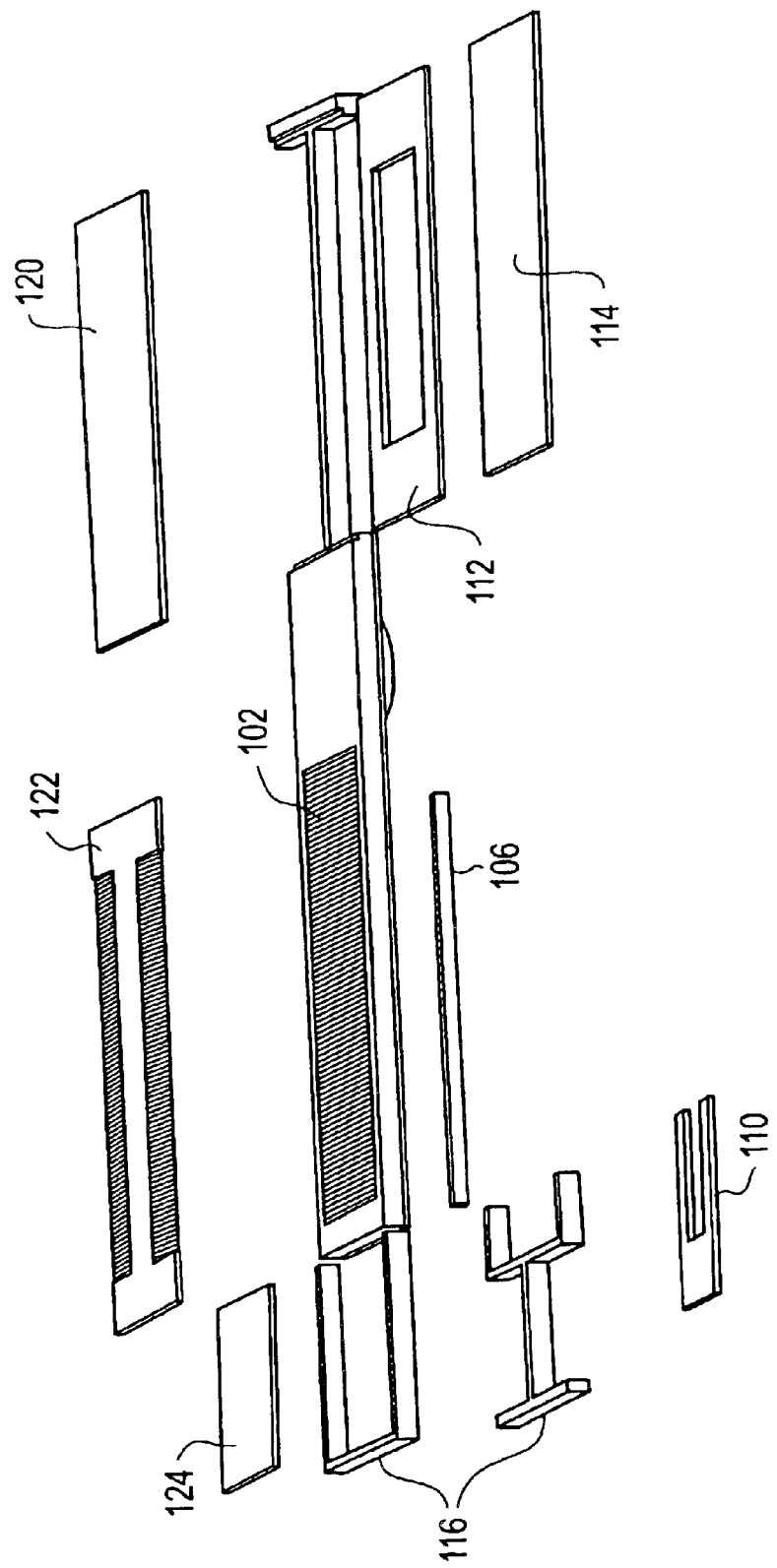
FIG. 10 is an exploded view of the tabletop showing additional supports and inserts that may be used with the frame of FIG. 2.

FIGS. 9 and 10 illustrate support systems that may be used with the frame 52 of FIG. 2. The tabletop frame 52 accepts various interchangeable panels, inserts, and other attachments, which when in place form part of the tabletop structure. These components are also designed so that only non-metal components are located within the beam area when the tabletop 50 is installed in the treatment device. Individual inserts are configured to position and immobilize a patient for accurate treatment. Referring first to FIG. 9, support platforms 100, 102, and 104 are configured to provide general planar surfaces for support of a patient on the tabletop frame 52. Support panels 100 and 102 rest on the lip formed by shoulder section 62 of the tubular frame members 60 (FIGS. 5 and 9). Panel 102 includes an open mesh racquet design as described below. Panels 100 and 102 may also be attached to frame 52 along one end so that they can pivot upwardly to raise the torso or legs of the patient.

Panel 104 is used to provide head support and may be installed on either end of the frame 52. Accessory rail 106 is pivotably mounted to the frame 52, at a pivot point located along the central section 54 of the tabletop so that it can be used at either end of the table and moved out of the way when it is not needed.

Referring now to FIG. 10, additional supports and inserts are shown. Inserts 110, 112, and 114 are shaped to immobilize various parts of the human anatomy with thermoplastic components attached thereto. Insert 116 is a frame for head extension insert 110 used for head and neck mobilization. A thermoplastic mold may be made of a patients head and attached to insert 110, which has holes designed to mate with openings in the mold to hold a patient in a repeated position for multiple treatments. Inserts 112 and 114 are used for prone pelvic treatment. These inserts may be placed on the T-section 56 of frame 52. Insert 120 may be used in place of insert 102 and includes an upper skin over the mesh design for stiffness and patient comfort. Insert 122 is used in place of insert 102 or 120 and includes a central solid portion with lateral mesh portions on each side. Insert 124 is another type of head extension support. It is to be understood that the inserts shown in FIGS. 9 and 10 are only examples, and many other types and configurations of supports, inserts, panels may be used with the tabletop frame 52 of FIG. 2. The supports may be constructed of layers of carbon fiber to form a solid insert, have a sandwich type construction, or a mesh construction as further described below. The thickness may be varied to achieve a desired stiffness for specific applications, while maintaining suitable transmission properties.

The supports may include base plates, breast boards, pelvic boards and other accessories. The supports may be configured to provide integrated immobilization capabilities to hold a patient in a specific position for repeated treatment and diagnostics. For example, the head and neck base plate can be used with molded head supports to immobilize the patient's head. The mold may be snapped and locked into the base plate. Importantly, the supports are integrated into the table (i.e., remain in place within the frame). This reduces the need for additional immobilization pieces and indexing of immobilization inserts. The panels are preferably configured so that one end of the panel can pivot upwardly relative to the frame to provide flexibility in positioning parts of the patient's body. Since the immobilization panels are set in place within the frame and ready for use in positioning a patient, the patient can easily be located in a prescribed position for administration of an x-ray beam for palliative and curative cancer diagnosis and treatment. The position of the integrated immobilization panels relative to the frame are also repeatable since they typically remain in place within the frame. Thus, improving accuracy and the reducing the need to place immobilization devices on top of the frame for each patient.

As previously discussed, the panels rest upon a lip formed by the shoulder section 62 of the tubular members 60 of the frame 52. An upper surface of the panels is preferably generally planar with an upper surface of the frame so that the panels rest within the frame. This eliminates the need to remove and replace the panels for different procedures since they are integrated into the tabletop. The frame 52 may also include a spring loaded pin mechanism that holds the panels in place. The spring-loaded mechanism is preferably attached to a handle that can be used to disengage the pin from an aligned opening within the side of the panel and release the pin so that the pin is inserted into the opening in the panel. The pin is preferably spring loaded so that it extends into the frame opening with no insert in place. The pin is retracted to install the insert and the pin automatically engages the hole in the insert. To remove the insert, a knob can be rotated to retract the pin to its open position. Other quick-release devices or fastening means may be used to hold the inserts in place. The quick-release device is preferably positioned at one end of the panel so that the other end of the panel is free to rotate upwardly relative to the frame.

Figure 11:
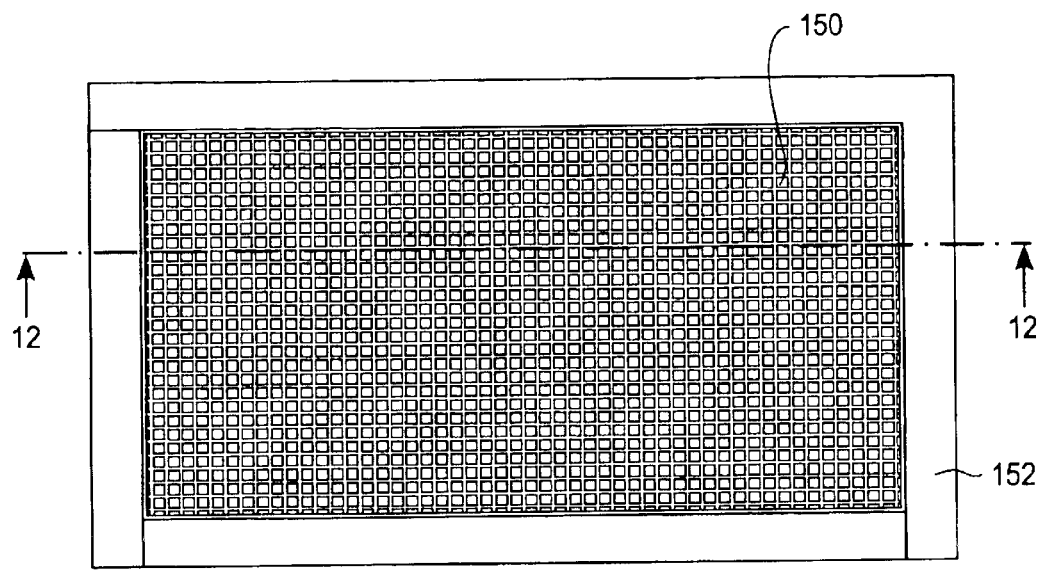
FIG. 11 is a plan view of a mesh support for use with the frame of FIG. 2.
Figure 12:
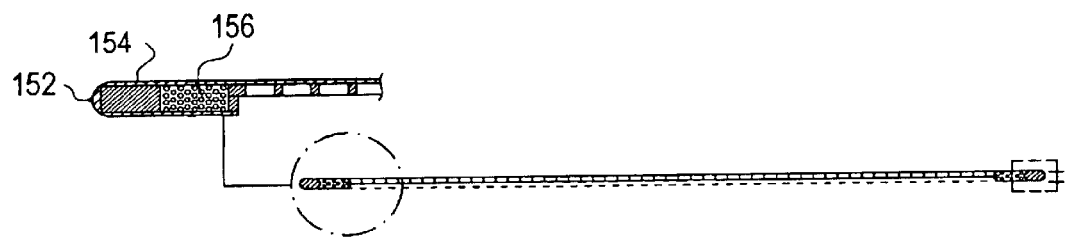
FIG. 12 is a cross-sectional view taken through line 12—12 of FIG. 11 and an enlarged view of an end portion of the mesh support.

The mesh racquet design of the support panels is shown in FIGS. 11 and 12. Grid pattern 150 is created by cutting adjacent squares from a carbon fiber panel using a high-pressure water jet cutting tool or milling process. The remaining weave material is laminated and preferably has a rectangular cross section to provide sufficient rigidity. In order to provide increased rigidity, a single layer of carbon skin may be laminated over the grid pattern (see insert 120 of FIG. 10). The upper surface of the insert is thus solid and the lower surface is open mesh. This provides an insert with improved rigidity while maintaining desired beam transmission properties of a mesh insert. The grid pattern 150 is preferably formed from a carbon fiber material and is surrounded by carbon fiber rods 152. The rod includes a carbon skin 154 and a filler 156, such as Rohacell 71. The carbon fiber rods 152 are glued to the grid pattern 150. As discussed above, a thin laminate skin may be attached to one or both surfaces of the grid pattern 150.

As can be observed from the foregoing, the present invention provides numerous advantages. The tabletop structure includes only non-metal components outside of the central rotation hub area. The design of the tabletop provides sufficient strength and stiffness while providing improved transmission in the beam projection areas. Furthermore, the weight of the frame is reduced from conventional metal frame tabletops.

Although the present invention has been described in accordance with the embodiments shown, one of ordinary skill in the art will readily recognize that there could be many variations to the embodiment and these variations would be within the spirit and scope of the present invention. Accordingly, many modifications may be made by one of ordinary skill in the art without departing from the spirit and scope of the appended claims.

What is claimed is:

1. A tabletop device for use in supporting and positioning a patient in a medical therapy or diagnostic system having a support base and operable to project a beam over at least a portion of the tabletop device, the tabletop device being configured for mounting on the support base, the tabletop device comprising:
    a central section configured for attachment to the support base, the central section positioned such that it is outside of a beam projection area when the tabletop is mounted in the medical therapy or diagnostic system;
    a frame fixedly attached to the central section and extending longitudinally outward from opposite sides thereof; and
    a support system connected to the frame for supporting a patient thereon;
    wherein at least a portion of the frame and support system is located within the beam projection area when the tabletop device is mounted in the medical therapy or diagnostic system and wherein the portion of the frame located within the beam projection area is formed substantially from non-metal components.

2. The device of claim 1 wherein the portion of the frame and support system located within the beam projection area is formed from composite material.

3. The device of claim 1 wherein the frame and support system is formed from a carbon fiber material.

4. The device of claim 1 wherein at least a portion of the support system is configured to provide high transmission of the beam.

5. The device of claim 1 wherein the frame is formed from carbon fiber.

6. A tabletop device for use in supporting and positioning a patient in a medical therapy or diagnostic system having a support base and operable to project a beam over at least a portion of the tabletop device, the tabletop device being configured for mounting on the support base, the tabletop device comprising:
    a central section configured for attachment to the support base, the central section positioned such that it is outside of a beam projection area when the tabletop is mounted in the medical therapy or diagnostic system;
    a frame fixedly attached to the central section and extending longitudinally outward from opposite sides thereof, the frame being formed of composite tubular members; and
    a support system connected to the frame for supporting a patient thereon;
    wherein at least a portion of the frame and support system is located within the beam projection area when the tabletop device is mounted in the medical therapy or diagnostic system and wherein the portion of the frame located within the beam projection area is formed substantially from non-metal components.

7. The device of claim 6 wherein the tubular members are connected with angles mounted within two adjacent tubular members.

8. The device of claim 7 wherein the angles are glued to an inner surface of the tubular members.

9. The device of claim 7 wherein the angles are formed from carbon fiber.

10. The device of claim 1 wherein the support system comprises a generally planar mesh member.

11. The device of claim 10 wherein the mesh member is a carbon mesh laminate.

12. The device of claim 10 wherein the mesh member comprises a carbon skin attached to an upper surface thereof.

13. The device of claim 10 wherein the mesh member is surrounded by a carbon fiber rod.

14. The device of claim 10 wherein the mesh member comprises a plurality of 10×10 mm openings.

15. A tabletop device for use in supporting and positioning a patient in a medical therapy or diagnostic system having a support base and operable to project a beam over at least a portion of the tabletop device, the tabletop device being configured the mounting on the support base, the tabletop device comprising:
    a central section configured for attachment to the support base, the central section positioned such that it is outside of a beam projection area when the tabletop is mounted in the medical therapy or diagnostic system;
    a frame fixedly attached to the central section and extending longitudinally outward from opposite sides thereof; and
    a support system connected to the frame for supporting a patient thereon, the support system comprising a multi-layer composite member which varies longitudinally in thickness to reduce beam interference in select areas;
    wherein at least a portion of the frame and support system is located within the beam projection area when the tabletop device is mounted in the medical therapy or diagnostic system and wherein the portion of the frame located within the beam projection area is formed substantially from non-metal components.

16. The device of claim 1 wherein the support system comprises a plurality of panels having openings for receiving immobilization attachments for positioning a patient on the tabletop.

17. A tabletop device for use in supporting and positioning a patient in a medical therapy or diagnostic system having a support base and operable to project a beam over at least a portion of the tabletop device, the tabletop device being configured for mounting on the support base, the tabletop comprising:

a central section configured for attachment to the support base, the central section positioned such that it is outside of a beam projection area when the tabletop is mounted in the medical therapy or diagnostic system;

a frame fixedly attached to the central section and extending longitudinally outward from opposite sides thereof;

an accessory rail pivotably mounted about a central axis extending generally perpendicular to the frame such that the rail can be positioned to extend along one of the edges of the frame extending from the central section of the frame; and a support system connected to the frame for supporting a patient thereon;

wherein at least a portion of the frame and support system is located within the beam projection area when the tabletop device is mounted in the medical therapy or diagnostic system and wherein the portion of the frame located within the beam projection area is formed substantially from non-metal components.

18. A system for use in medical therapy or imaging, the system comprising a base, a tabletop mounted on the base for supporting a patient, a beam projection device operable to project a beam over at least a portion of the table, the tabletop comprising:

a central section configured for attachment to the support base, the central section positioned such that it is removed from a beam projection area when the tabletop is mounted in the medical therapy or imaging system;

a frame fixedly attached to the central section and extending longitudinally outward from opposite ends thereof; and a support system connected to the frame for supporting a patient thereon;

wherein at least a portion of the frame and support system is located within the beam projection area when the tabletop is mounted in the medical therapy or imaging system and wherein the portion of the frame located within the beam projection area is formed from non-metal components.

19. The system of claim 18 wherein the frame and support system is formed from composite material.

20. A system for use in medical therapy or imaging, the system comprising a base, a tabletop mounted on the base for supporting a patient, a beam projection device operable to project a beam over at least a portion of the table, the tabletop comprising:

a central section configured for attachment to the support base, the central section positioned such that it is removed from a beam projection area when the tabletop is mounted in the medical therapy or imaging system;

a frame fixedly attached to the central section and extending longitudinally outward from opposite ends thereof, the frame comprising tubular members formed from a composite material; and a support system connected to the frame for supporting a patient thereon;

wherein at least a portion of the frame and support system is located within the beam projection area when the tabletop is mounted in the medical therapy or imaging system and wherein the portion of the frame located within the beam projection area is formed from non-metal components.

21. The system of claim 20 wherein the tubular members are connected with angles mounted within two adjacent tubular members.

22. The system of claim 18 wherein the support system comprises a generally planar mesh member.

23. The system of claim 22 wherein the mesh member is a carbon mesh laminate.

24. The system of claim 22 wherein the mesh member comprises a carbon skin attached to an upper surface thereof.

25. The system of claim 18 wherein the support system comprises a plurality of panels having openings for receiving immobilization inserts for positioning a patient on the tabletop.

26. A system for use in medical therapy or imaging, the system comprising a base, a tabletop mounted on the base for supporting a patient, a beam projection device operable to project a beam over at least a portion of the table, the tabletop comprising:

a central section configured for attachment to the support base, the central section positioned such that it is removed from a beam projection area when the tabletop is mounted in the medical therapy or imaging system;

a frame fixedly attached to the central section and extending longitudinally outward from opposite ends thereof;

an accessory rail pivotably mounted about a central axis extending generally perpendicular to the frame such that the rail can be positioned to extend along one edge of the frame extending from the central section of the frame; and a support system connected to the frame for supporting a patient thereon;

wherein at least a portion of the frame and support system is located within the beam projection area when the tabletop is mounted in the medical therapy or imaging system and wherein the portion of the frame located within the beam projection area is formed from non-metal components.

27. A system for use in medical therapy or imaging, the system comprising a base, a tabletop mounted on the base for supporting a patient, a beam projection device operable to project a beam over at least a portion of the table, the tabletop comprising:

a central section configured for attachment to the support base, the central section positioned such that it is removed from a beam projection area when the tabletop is mounted in the medical therapy or imaging system;

a frame fixedly attached to the central section and extending longitudinally outward from opposite ends thereof; and a support system connected to the frame for supporting a patient thereon, the support system comprising a plurality of integrated immobilization devices;

wherein at least a portion of the frame and support system is located within the beam projection area when the tabletop is mounted in the medical therapy or imaging system and wherein the portion of the frame located within the beam projection area is formed from non-metal components.

28. A tabletop device for use in supporting and positioning a patient in a medical therapy or diagnostic system having a support base, the tabletop device being configured for mounting on the support base, the tabletop device comprising:
- a central section configured for attachment to the support base,
- a frame attached to the central section in a fixed position and extending longitudinally outward from opposite sides thereof; and
- a support system integrally mounted within the frame, the support system comprising immobilization panels configured for immobilizing portions of a patient's body on the tabletop device.

29. The device of claim 28 wherein the immobilization panel includes a pelvic immobilization panel.

30. The device of claim 28 wherein the immobilization panel includes a head and neck base plate.

31. The device of claim 28 wherein the immobilization panel includes a breast board.

32. The device of claim 28 wherein the immobilization panel is pivotably attached at one end to the frame such that the other end of the panel is free to rotate upwardly from the frame.

33. The device of claim 28 wherein the immobilization panel is attached to the frame with a quick release device.

34. A tabletop device for use in supporting and positioning a patient in a medical therapy or diagnostic system having a support base, the tabletop device being configured for mounting on the support base, the tabletop device comprising:
- a central section configured for attachment to the support base,
- a frame fixedly attached to the central section and extending longitudinally outward from opposite sides thereof; and
- a support system integrally mounted within the frame, the support system comprising immobilization panels configured for immobilizing portions of a patient's body on the tabletop device;
- wherein the immobilization panel is attached to the frame with a spring loaded pin.

35. A tabletop device for use in supporting and positioning a patient in a medical therapy or diagnostic system having a support base, the tabletop device being configured for mounting on the support base, the tabletop device comprising:
- a central section configured for attachment to the support base,
- a frame fixedly attached to the central section and extending longitudinally outward from opposite sides thereof; the frame comprising a plurality of members extending at least partially around a periphery thereof, the members having a lip on an internal edge thereof for receiving the immobilization panel; and
- a support system integrally mounted within the frame, the support system comprising immobilization panels configured for immobilizing portions of a patient's body on the tabletop device.

36. The device of claim 28 wherein the immobilization panel is configured such that an upper surface thereof is generally planar with an upper surface of the frame when the immobilization panel is in place within the frame.

37. The device of claim 28 wherein the frame and support system are formed from non-metal components.

* * * * *